(12) United States Patent
Ferreira et al.

(10) Patent No.: US 6,718,077 B1
(45) Date of Patent: Apr. 6, 2004

(54) METHOD AND DEVICE FOR THE DETECTION OF MICROORGANISMS BY FIBER OPTICS

(75) Inventors: Aldo P. Ferreira, Rio de Janeiro (BR); Ricardo M. Ribeiro, Rio de Janeiro (BR); Marcelo M. Werneck, Rio de Janeiro (BR)

(73) Assignees: Fundacao Oswaldo Cruz - Fiocruz; Universidade Federal do Rio de Jandiro-UFRJ (BR)

( * ) Notice: Subject to any disclaimer, the term of this patent is extended or adjusted under 35 U.S.C. 154(b) by 412 days.

(21) Appl. No.: 09/629,830

(22) Filed: Jul. 31, 2000

(30) Foreign Application Priority Data

Jul. 21, 2000 (BR) .......................................... 10003066

(51) Int. Cl.$^7$ .............................. G02B 6/00; C12Q 1/04
(52) U.S. Cl. .......................................... 385/12; 435/34
(58) Field of Search ................ 385/12, 13; 250/227.11; 435/29, 34, 288.7

(56) References Cited

U.S. PATENT DOCUMENTS

| | | |
|---|---|---|
| 4,242,447 A | 12/1980 | Findl et al. |
| 4,447,546 A | 5/1984 | Hirschfeld |
| 4,558,014 A | 12/1985 | Hirschfeld |
| 5,631,170 A | 5/1997 | Attridge |
| 5,809,185 A * | 9/1998 | Mitchell ..................... 385/12 |
| 5,866,430 A * | 2/1999 | Grow ......................... 436/172 |
| 6,197,576 B1 * | 3/2001 | Eden ......................... 435/288.7 |
| 2003/0003527 A1 * | 1/2003 | Shimakita et al. ............. 435/34 |

* cited by examiner

Primary Examiner—Hemang Sanghavi
(74) Attorney, Agent, or Firm—Nixon & Vanderhye PC

(57) ABSTRACT

The detection/monitoring of microorganisms present in a sample is enabled through the use of a fiber optic biosensor with an evanescent-field. Embodiments include: (i) a method for detection of contamination by specific microorganisms through the use of said biosensor, permitting the interaction of the exposed evanescent-field with the sample to be examined which has a form adequate to obtain the generation of an optical signal in response to the presence of microorganisms in said sample; (ii) a composition for use in the detection of microorganisms; and (iii) a device for surveying microorganisms through an insertion of a sensitive fiber optic, with an adequately exposed evanescent-field, into a surface or volume of a biological culture medium specific for the microorganism to be detected, comprising a demodulation system based on a fiber optic circuit and related components.

27 Claims, 8 Drawing Sheets

METHOD AND DEVICE FOR THE DETECTION OF MICROORGANISMS BY FIBER OPTICS

The present invention refers to a method and device for the detection of microorganisms using a combination of microbiological procedures with devices constructed with fiber optics and related components.

The microbiological procedures enable the microorganisms to be selectively cultivated and these, when in physical contact with a conveniently constructed fiber optic circuit, permit the detection and monitoring of the microorganisms in a fast and accurate way.

BACKGROUND OF INVENTION

Microorganisms are life forms that despite their micrometrical size scale significantly affect human life. They may constitute viruses, bacteria, fungi, protozoa and algae. They are present in solids, liquids and air; and in all cases it may be of vital interest or importance to detect the specific presence and/or to monitor, qualitatively or quantitatively, the growth over time of one or more of these microorganisms. Many of them are of use to various types of industries, such as food industries, brewery, viticulture, pharmaceutical, etc., for the catalysis of many biochemical reactions of commercial interest, amongst others. Other microorganisms do not seem to serve any other practical purpose, but are, in principle, harmless to human health. However, some of these microorganisms may become dangerous, for a series of reasons, after undergoing certain types of biological transmutations and whereupon they are termed pathogenic. These pathogens may exist and develop in various environments. Other types of microorganisms may be intrinsically dangerous, meaning that they are naturally constituted as noxious to human health. Overall, the presence and the concentration of some of the referred microorganisms directly affect: (i) the quality (potability and suitability for bathing)of the water for consumption in major urban centers and seaside resorts, possibly causing a series of diseases, such as diarrhea; (ii) the quality of food, which may generically cause food poisoning, and, particularly, "hamburger disease" and (iii) the quality of air in clinics, outpatients and hospitals where the presence of aerobiological microorganisms constitutes, for example, an important vector for hospital infections. In any of these cases, it may be of great interest or vital importance to detect the presence of certain microorganisms in real time or almost immediately, and consequently to monitor their evolution over time aiming to infer some useful information. At present, the conventional techniques for surveying microorganisms are closely linked to laboratory and outpatient procedures and based in selective biological culture and in the use of microscopy for direct visual observation. These techniques are reasonably complex, as they demand from the operator significant intervention and skill in order to obtain dependable results, and typically require 1 to 10 days for completion. This means that the conventional techniques require an average of 72 h between the capture of the microorganism, its isolation, identification and consecutive monitoring of its evolution over time. The standard procedures concerning bacteriological tests are furnished by the American Public health Association (APHA). All these procedures require incubation in a culture medium to produce an adequate supply of microorganisms for various analyses at the end of the test. Apart from which, the conventional techniques use equipment that is not particularly low cost, making its employment difficult or unviable for widespread surveying, in other words, for detection/monitoring of microorganisms in more than one place simultaneously.

There are other more modern procedures concerning biological detection, such as: radiometry, electrochemicals, chromatography, chemiluminescence, pulse field electrophoresis and fluorescence. Concerning the techniques mentioned, there are some practical restrictions such as, for example, their success is highly dependent on the quantity of bacteria that can be concentrated in the test sample. This procedure, generally, requires a minimum of $10^4$ bacteria. In molecular reactions, the test procedures are particularly liable to cross contamination by other molecules or molecular fractions.

In addition, optical preventive techniques can be employed, aiming the elimination of pathogenic microorganisms, highlighting, for example, the use of ultraviolet light as a germicide, avoiding the infection of a determined environment or a material medium. On the other hand, the medical knowledge for fighting pathogenic microorganisms that had already infected the human body, especially those originating from hospital infection, food poisoning and water contamination, is vast but incomplete. Such microorganisms may also become resistant to any known drug due to their possible biological mutations. Recently, some success has been achieved with patients infected with these microorganisms using photochemical drugs activated by electroluminescent semiconductor diodes of high optical power with the correct wave length, permitting the total elimination of these microorganisms, without, in principle, harming the patient. This is the case, for instance, of the procedures recently developed and described by Pearce et al (H Pearce, M. Messager and J. Y. Maillard. "Effect of biocides commonly used in the hospital environment on the transfer of antibiotic-resistance genes in *Staphylococcus aureus*". J.Hosp. Infect. 43.2, pp. 101–107, 1999).

The optical surveying of microorganisms, which is the object of the invention herein, finds its place between the preventive techniques for the reduction/elimination of microorganisms and the techniques that aim to eliminate pathogens that have already infected the patients.

The essential characteristics of any biological sensor are its selectivity, sensitivity, resolution and response time, characterized by reactive recognition based on the type of test and the choice of detection technique. At a second level, there must be a biological surveying technology available that is robust, practical and of low cost, so that it may be employed in the field. Presently, various techniques and correlated devices are available, many of these are still at laboratory level whilst others are commercial, all aiming the detection and monitoring of microorganisms.

Microscopy, as already mentioned, constitutes a fundamental analysis tool in microbiology, not only for the detection/monitoring of microorganisms, but also for the basic study of these. In the same way, there is a method of surveying bacteria involved in processes of hospital infections presently in use, known as pulsed field electrophoresis in, which is capable of tracking with precision the microorganisms involved, mapping and evaluating the level of environmental impact. However, it presents the disadvantage of the analysis taking approximately 7 to 14 days, as described by Birron and Lai (B. Birron and E. Lai. "Pulsed field electrophoresis: a practical guide". Academic Press, San Diego, 1993).

With the aim of undertaking microbiological detecting and monitoring in an automatic and selective manner, the concept of the biosensor arises. A biosensor may be understood as a discreet electrical and/or optical component built based on the integration of biological materials with inorganic materials. A biosensor, in practice, is therefore capable of producing an analog electrical or optical signal when placed in contact with some specific subject, whether by its presence or any chemical-biological alterations occurring from it. A biosensor may be considered as a biologically active element, however, it requires connection, in some form, to a larger configuration, so that the electrical or optical analog can be adequately demodulated. The set-up thus formed is called a biological sensor. Fiber optics, in a general manner, may be used in the construction of biosensors, which means that through some appropriate technique, biological materials should be integrated to the sheath or core of the fiber (generally of glass or plastic) composing, therefore, an optical biosensor. In this manner, the light propagating through the core of the fiber can interact with the biological material (an antibody, for instance) integrated through a coupling by evanescent-field. The evanescent wave biosensor can induce modulation of intensity, complete phase, wave length or polarization of the propagating optical signal, or a fluorescent signal can be generated in function of a photo-biological reaction where part of the energy of this signal propagates itself through the optical fiber. Evanescent-field biosensors are described in the state of the art (J. S. Schultz. "Biosensors". Scient. Amer. pp. 64–69, 1991.; J. P. Golden, G. P. Anderson, R. A. Ogert, K. A. Breslin and F. S. Ligler. "An evanescent wave fiber optic biosensor: Challenges for real world Sensing". SPIE. 1796. 1992. pp. 1–8; S. P. J. Higson and P. M. Vadgama. "Development o an evanescent wave fiber optic biosensor. Med. & Biol. Eng. & Comp. 32.1994. pp. 601–609).

Biological sensors based on evanescent wave are, in a general manner, dependent on a combination of various technologies of biological, physical and chemical natures. In this sense, the North-American patents U.S. Pat. No. 4,447, 546 and U.S. Pat. No. 4,558,014 describe the techniques of spectroscopy by total reflection (TRS), where the use of evanescent wave to excite a fluorescently linked analytic and, consequently, detect the resultant fluorescence is claimed. Other patents describe methods to improve measurement precision. This is the case of patent U.S. Pat. No. 5,631,170. The method involves marking the biosensor with fluorescent antibodies, in other words, antibodies linked to dye molecules. Provided that the antibodies mentioned are not linked to the antigens (subject), the dye molecules will not be excited by the evanescent-field. However, when the biosensor is in the presence of the specific antigen to be detected, the propagating light will be capable of inducing fluorescence in the dye molecules. Another method is that which is described in patent U.S. Pat. No. 4,242,447, that bases itself on the detection and quantification of bacteria in a liquid sample characterized by fact that this sample contains an agent capable of inducing the production of an enzyme in the bacteria. This enzyme shall be capable of reacting with a fluorescent conjugate ingested by the bacteria, in such a manner as to release its fluorescent part, and this total fluorescence is measured and compared to the total of bacteria present in the medium.

However, as previously mentioned, there is an urgent need for the development of a method for detecting microorganisms that is sensitive and has a quick response, without the inconvenients already mentioned, such as: necessity of a minimum of $10^4$ bacteria, cross contamination by other molecules or molecular fractions and minimum average time of 72 h between capture of the microorganism and the monitoring of its evolution over time.

Thus, aiming to achieve this objective; a strategy of combining biological procedures with a fiber optic sensor with an evanescent-field was used, capable of detecting the microorganisms 4 to 5 times faster than when employing conventional procedures.

SUMMARY OF INVENTION

The aim of the present invention is the detection/monitoring of microorganisms found in air, water or foodstuffs, through the use of a fiber optic biosensor with an evanescent-field.

A first concretization of the present invention concerns a method for the detection of specific microorganisms through the application of an evanescent-field of a sensitive optical fiber, characterized by the stages:

(a) exposing the evanescent-field of the sensitive fiber optic using an appropriate technique based on physical and chemical properties;

(b) permitting immediate contact of the exposed evanescent-field obtained in the stage (a) with the sample to be examined, with the aforementioned sample having a form adequate so as to obtain the generation of an optical signal in response to the presence of microorganisms in the sample;

(c) demodulating the optical signal generated in stage (b) and using this value to quantify the microorganisms through an appropriate method.

In a second concretization, the invention is directed to a composition for use in the detection of microorganisms characterized by incorporating a selective culture medium for microorganisms needing to be detected and reactants capable of altering the properties of the medium in a manner as to favor the interaction of the system fiber-microorganism.

In a third concretization the invention refers to a device for surveying microorganisms through the insertion of a sensitive fiber optic (11), with an adequately exposed evanescent-field, into a surface or volume of a biological culture medium (12) specific for the microorganism to be detected, comprising a demodulation system based on a fiber optic circuit and related components.

DETAILED DESCRIPTION OF THE INVENTION

Figure 1:
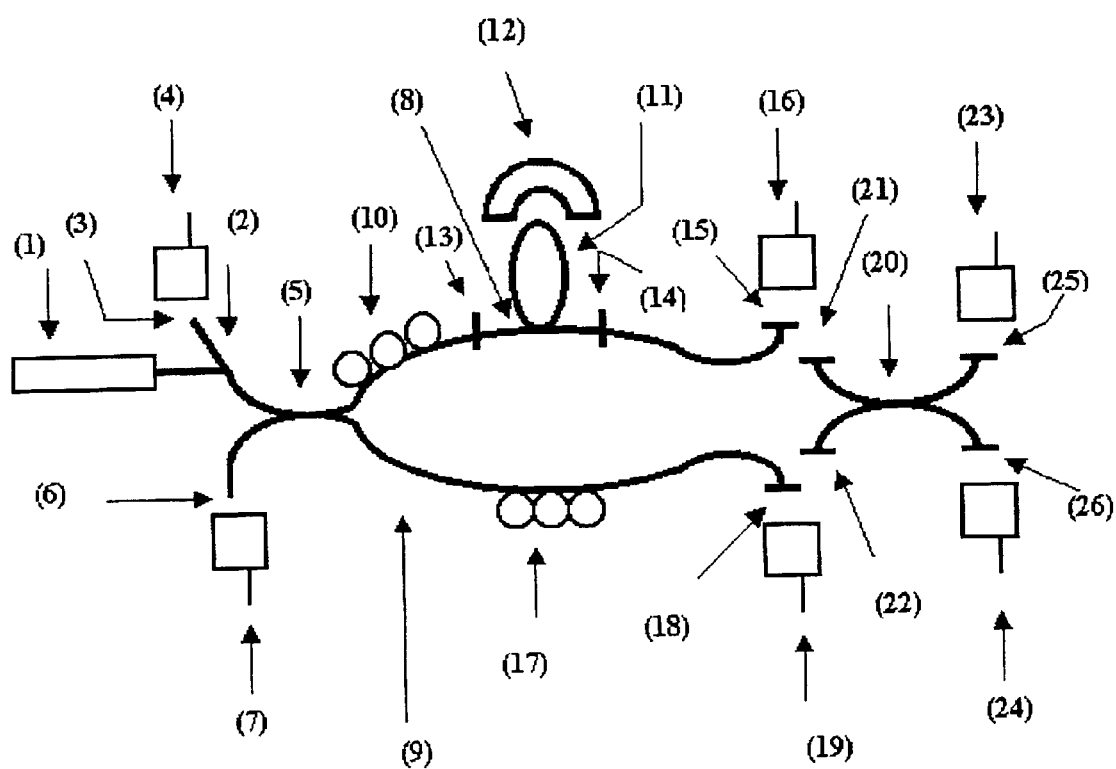
FIG. 1: Shows the preferential assembly of the device for the detection of microorganisms through fiber optics employed in the present invention.

With the purpose of resolving the existing inconveniencies in the state of the art, the present invention provides a sensor for microorganisms based on a technology composed of microbiological procedures combined with a fiber optic device.

The microbiological procedures consist in permitting the growth of a selective culture of a determined microorganism in an adequate support such as, for example, a Petri dish or a slide where the medium is composed of nutrients appropriate to the growth and viability of the microorganism and their quantity, pH and temperature are precisely controlled. The choice of the selective culture medium will depend on the microorganisms to be monitored being, however, of common knowledge to experts in the field. The optimization of the culture medium shall be undertaken with specific nutrients, such as: substance(s) source(s) of nitrogen, for instance industrial residues rich in protein, soya protein, urea, yeast extract; (ii) substance(s) source(s) of carbon, for instance manitol, dextrose, sacharose; and substance(s) source(s) of micronutrients, selected from, for instance, mixtures of salts involving $MgSO_4$, $MnSO_4$, $ZnSO_4$, $FeSO_4$ and $CaCl_2$. As an option, it is possible to use reactants that are capable of altering the properties of the culture medium in a manner as to permit the index of refraction of the subject to be better detected. In other words, these reactants will favor the fiber-microorganism interaction. In this manner, it is possible to have a composition containing selective culture medium for the microorganism chosen for detection and reactants capable of altering the culture medium so as to permit the index of refraction of the subject to be better detected.

On the surface or inserted in a volume of the aforementioned biological culture medium is a segment of optical fiber termed sensitive fiber optic that is then in direct physical contact with the subject.

The basic geometric structure of an optical fiber consists of a concentrically cylindrical core and sheath. Light is propagated through the core, being almost entirely spatially combined there, which characterizes one or more means of transversal optical propagation. Basically, what ensures the confinement and the propagation of light in an optical fiber is the fact that its core possesses an index of refraction that is superior to the sheath, as it permits the occurrence of the total internal reflection phenomena. An optical fiber may support the propagation of only one mode (monomode fiber) or two or more modes (multimode fiber). In either of the cases a part of the propagating luminous energy always extends beyond the sheath decreasing in amplitude in an exponential manner along the radial co-ordinates. This part of light that extends beyond the sheath is termed evanescent-field. The sheath of an optical fiber may already be sufficiently thin, or have its thickness decreased in such a manner, that the evanescent-field becomes exposed externally, in other words, in a manner that permits that the light suffers the phenomena of optic tunneling through the sheath and can interact with the outside environment.

Alternatively, the sheath of the optic fiber may be completely removed so as to directly expose its core. In this last case, the external medium alone assumes the role of the sheath. In either of the two cases, light may to a greater or lesser degree interact with the subject (external medium)and this phenomena is termed evanescent-field coupling. A sensitive fiber consists therefore of a segment of optical fiber which is placed in contact with the surface of a biological medium, where the evanescent-field may be accessed externally and the propagating light interacts with this biological medium. The presence, growth and/or reproduction of microorganisms in the culture medium dynamically alter its optical constants. This means that from the moment that the microorganisms are inoculated in culture medium it starts, in a general manner, to have its coefficient of attenuation and index of refraction varying with time and the surface or volume of the biological mass. The evanescent-field extends in significant amplitude which characterizes a volume of light-microorganism interaction.

In the light-microorganism interaction, the optical signal through its evanescent-field shall, in a general manner, experience a temporal variation of the average index of refraction (component DC) and the attenuation coefficient due to the intrinsic absorption of the medium and spreading (Mie) because of spatial fluctuations (component AC) of the index of refraction generated by the presence of each microorganism.

As such, when the microorganism starts its growth along the length of the optical fiber two effects may occur: (i) during the lag phase, due to the metabolism of the microorganism (for instance, bacteria) enzymes are released that cause an alteration of the index of refraction and/or (ii) due to an increase in the number of microorganisms in contact with the optical fiber, during the log phase, the medium turns opaque with time. In this manner, the intrinsic absorption also suffers alterations. Therefore, the reduction of the optical power is intimately related with the number of microorganisms present in the volume occupied by the evanescent-field around the fiber.

Therefore, the light propagated through the sensitive fiber simultaneously interacts with the microorganisms present and/or in evolution that are within the volume of interaction by coupling of the evanescent-field. In this manner, the actual mechanism of surveying occurs, where the optical signal is modulated in function of the temporal variations of the optical constants. Therefore, the presence and/or evolution of the microorganisms affects some characteristics of the light guided through the sensitive optical fiber. The characteristics of light that may be affected individually or in a combined manner are: amplitude (intensity), complete phase, wavelength or polarization. As can be seen in FIG. 1, the sensitive fiber is inserted continuously (in-line) in an adequately constructed fiber optic circuit where the optical signal bearing information from the subject can be demodulated during the course of the biological culture. Some possible optical circuits are shown in FIG. 1 and can demodulate signals that have been modulated at the propagation by the sensitive optical fiber by: average optical power (amplitude or intensity), complete phase (advance or delay of the phase), reflected and/or transmitted spectrum (wave-length), polarization and shape/temporal or spectral parameterisation of optical pulses. In this manner, it is possible to indirectly detect the presence of and/or temporally monitor the microorganisms, eventually inferring additional information such as, for instance, the initial concentration of microorganisms, in the case of the sensor being calibrated beforehand.

The present invention consists, preferably, of an available material medium where possibly microorganisms may exist and/or be cultivated selectively. This material medium may constituted of a biological gel within a Petri dish in a manner as to permit that microorganisms be cultivated on the surface of the aforementioned gel. Preferably, an agent may be added to the culture medium that permits the maintenance of the residual humidity favoring thus, a better interaction between the microorganisms and the sensitive area. More preferably, this agent is glycerol in an appropriate concentration.

This material medium may also be constituted of fluids of a corporal nature such as water, blood, urine, etc. In this last case, microorganisms may be present and reproduce throughout the volume of the fluid. The segment a of sensitive optical fiber should be conveniently placed on the surface or inserted in the volume of the biological culture medium. Beforehand, however, this fiber shall have an area of its primary covering removed and will undergo a treatment employing an appropriate technique based on chemical and physical properties. This treatment aims to expose the evanescent-field of the optical fiber through etching, for instance, using, preferably, strong acids, such as hydrdfluoric, hydrochloric, sulfuric acids, for instance. It is necessary that the treatment lasts for the time necessary to etch the sheath of the optic fiber to an approximate thickness of 0.5 to 1 $\mu$m from the core. In this way, it is possible to expose approximately 80% of the evanescent-field. The etching is interrupted by the immersion of the fiber in deionised water and, afterwards, in a pH stable solution for an adequate time to remove any residue of water. Thus, it is possible to couple the evanescent-field of the means of guided propagation to the material medium containing the subject (microorganisms). The sensitive fiber optic, in turn, is inserted continuously in a larger fiber optic circuit, having a particular assembly with the aim of demodulating the optical signal modulated by the subject. These characteristics confer to the invention operational advantages of biological selectivity, sensitivity, resolution, response velocity, stability, possibility of miniaturization, ease of operation and easy incorporation into larger and more complex optical circuits that are destined to compose a survey network (overall survey) in a manner that microorganisms may be detected/monitored in various places simultaneously. The sensor technology described here should be employed preferably for biological detection/monitoring in a qualitative and/or quantitative manner having a specific microorganism as subject.

The present invention may be employed, for instance, in the detection/monitoring of aerobiological pathogens encountered in hospital, outpatients and clinic environments, in the bacteriological verification of foodstuffs in general, and in samples intended for verification of water quality.

The preferred arrangement for the invention described herein, acting as a sensor for microorganisms, may be constituted in various possible assembly as illustrated in FIG. 1. The preferred arrangement does not exclude the possibility that the sensitive fiber optic apart from the core and sheath, may have incorporated to it one or more concentric layers of dielectric, metallic, semiconductor or superconductor materials with the end of altering the transversal spatial distribution of the evanescent-field and therefore optimizing the coupling with the biological medium and thus the performance of the sensor. More preferably, the interaction bacteria-fiber may be favored coating the fiber with a polymer film such as, for instance, polyvinyl chloride, polyurethanes, polyureas, and polyesters. In addition, the sensitive optical fiber may contain the engraving of a Bragg grating that works like a spectral filter. The Bragg gratings engraved in optical fibers are well described in Kashyap (Raman Kashyap. "Fiber Bragg Gratings". Academic Press, 1999) and are constituted by an axial modulation in the index of refraction of the core in lengths of, typically, millimeters or centimeters. Thus, part of the spectrum entering the Bragg grating shall be reflected by the fiber whilst the remaining spectrum shall be transmitted. Modulation of the wave length will be generated when changes in the index of refraction experienced by the propagating light in the sensitive fiber optic occurs. One means of obtaining this is well described by Ribeiro et al (R. M. Ribeiro et al. "All-optical control of Bragg grating in semiconductor coated D-shaped fiber". Optics Letters. 24.7. pp. 111–113, 1999) where the light interacts simultaneously with the Bragg grating and some material medium whose index of refraction suffers changes. The sensitive optical fiber may also be constituted as a fiber with a high birefringency (HiBi) such as, for instance, a fiber maintaining polarization. In this manner, the propagating light experiences two different indexes of refraction in directions orthogonal to each other. In the case of the index of refraction of the subject as experienced by the evanescent-field suffers changes, light polarization shall be modulated. The sensitive optical fiber, as well as being of the polarization maintaining type, may also contain an engraved Bragg grating. In this case, it will be possible to obtain the modulation in the wave length and the polarization simultaneously. The preferred arrangement also does not exclude the possibility that the sensitive optical fiber may be inserted in some other type of assembly (fiber optic circuit for demodulation) not described by this patent. The optical fiber(s) used whether for the construction of the optical circuit for demodulation or for the making of the sensitive fiber may be manufactured using as raw material silica ($SiO_2$) and other glass in general, plastics of various types (polymers) or any other material medium with a sufficient optical transparency.

FIG. 1 shows the diagram of the preferred assembly of the present invention, in other words, the implementation of survey technology for microorganisms by fiber optics. An optical source (1) that may be constituted by an electrical luminescent diode (LED) or a semiconductor laser (LD), possesses the function of generating light in a continuous mode, modulating or pulsing, that shall be used in the circuit of the microorganism survey. The light produced by the optical source is applied to the circuit through a fiber optic coupling of the 2×1 type (2), also called a WDM coupling. The other source of entry (3) of the 2×1 coupling is constituted, in reality, by an exit, so that the light processed by the survey device may be detected by the photodetector (4). This photodetector is preferably constituted by a semiconductor of the photodiode or phototransistor type, which functions in the electrical domain whereby light is transformed into a photocurrent. The coupling (2) is linked by fusion or mechanical connection to another 2×2 coupling to the optical fiber (5), also termed bidirectional coupler. The other source of entry (6) of the 2×2 coupling is constituted, in reality, by an exit, so that the light processed by the survey device may be detected by the photodetector (7). This photodetector is preferably constituted by a semiconductor of the photodiode or phototransistor type. The exit of the coupling (5) is linked by fusion or mechanical connection to the two extensions of optical fiber, one is termed sensitive extension (8) and the other is termed reference extension (9). Part of the optical fiber of the sensitive extension (8) may be coiled around a certain number of rings of a certain diameter, so as to constitute a polarization controller (10) of the propagating light. The sensitive optical fiber (11) is linked by fusion or mechanical connection in a manner as to provide continuity to the sensitive extension (8) of the optical circuit for survey. This fiber permits that the evanescent-field be accessed when put in direct physical contact with some biological medium (12). The sensitive optical fiber may be connected at extremities (13) and (14) to the rest of the optical circuit, termed demodulation circuit. The exit (15) of the sensitive extension (8) allows the light processed by the device to be detected by the photodetector (16). This photodetector will be constituted, preferably, of a semiconductor of the photodiode or phototransistor type. The other exit of the coupling (5) shall be linked by physical or mechanical connection to the reference extension (9), where part of the optical fiber that constitutes it is coiled around another polarization controller (17). The exit (18) of the reference extension (9) allows the reference light of the device to be detected by the photodetector (19). This photodetector will be constituted, preferably, of a semiconductor of the photodiode or phototransistor type. The light processed by the survey device emerges from the exit (15) and is detected by the photodetector (16). This photodetector will be constituted, preferably, of a semiconductor of the photodiode or phototransmitor type. The reference light emerges from the exit (18) and is detected by photodetector 19. In this manner, the device functions based on the modulation of the intensity (amplitude) of light. The 2×2 fiber optic coupling (20) possesses two entries (21) and (22). The exit (15) of the sensitive extension (8) may be directly linked or mechanically connected to the exit (18) of the reference extension (9). In this case, the device formed shall be a Sagnac fiber optic interferometer where the photodetector (4) detects the reflected optical signal whilst the photodetector (7) detects the optical signal transmitted by the device. If the exits (15) and (18) were to be reflective in a manner that light were at both extremities, the device formed will be a Michelson fiber optic interferometer where the photodetectors (4) and (7) will detect the processed optical signal. The links (13) and (14) can merely be done through the use of mechanical connections. In this case, the cleaved extremities of the sensitive optical fiber (11) may be semi-reflective, so that a fraction of the light may undergo multiple reflections in the sensitive optical fiber (11). In this manner, the device form shall be a Fabry-Perot fiber optic interferometer, where the signals shall be by photodetector (16) e (19). The exits (15) and (18) may be linked by fusion or mechanical connection to the entries (21) and (22), respectively, of the coupling (20). In this case, the device formed shall be a Mach-Zehnder fiber optic interferometer, where the signals shall be detected by photodetectors (23) and (24) after emerging from extremities (25) and (26) of the optical fiber.

The present invention is described in detail by the examples presented below. It is necessary to mention that the invention is not limited to these examples, but also includes variations and modifications within the limits of which it works.

EXAMPLE 1

Exposure of the Evanescent-field

So as to allow the exposure of the evanescent-field, 20 cm of a multimode optical fiber, of graded-index, with a diameter of 62.5/125 $\mu$m is attacked by a hydrofluoric acid solution at 38%, during 11 minutes. In this manner, the etching of the fiber optic sheath occurs to an approximate thickness of 0.5 to 1 $\mu$m from the core. After this period, the chemical reaction is interrupted by immersion in deionised water and, afterwards, in a phosphate buffered saline solution, pH 7.4, for 15 minutes. This fiber shall be, then, placed in the support containing the medium in which the microorganisms are growing.

EXAMPLE 2

Obtaining an Air Sample

An air sample is collected through the technique known to experts in the field as impaction-on-a-gel employing Merck MAS-100 equipment. In this manner, a sample of the ambient air was aspirated, through perforated plates, with the aid of a vacuum pump (with a is volumetric flow rate of 100 liters per minute) for 30 seconds. The resulting air stream that carries particles with diameters inferior to 10 $\mu$m, was directed to the agar surface of a Petri dish. Eighteen collections were undertaken, during six random days, three collections per day, during two weeks. During the three first days, a specific culture medium for *Staphylococcus aureus* was used, and during the three remaining days, a specific medium for *S. pneumoniae* was used.

EXAMPLE 3

Growth of Microorganisms in a Selective Culture Medium

The culture medium used for *Staphylococcus aureus* resistant to methicillin (MRSA) obtained in Example 2 was the Baird-Parker Agar (Difco Laboratories-Difco 0768-17-3) at an incubation temperature of 35° C. For *S. pneumoniae*, the culture medium used was Trypticase soya agar (Difco Laboratories, Detroit, Mich.—Difco 0026-17-1) supplemented with sheep blood at 5% at an incubation temperature of 35° C. In both the culture media glycerol at 0.2% was added, so as to avoid drying out the culture during the tests. For the growth of *E. coli* 0157:H7, the selective culture medium employed was the MacConkey sorbitol agar base (Difco Laboratories-Difco 0079-17-7), at an incubation temperature of 35° C.

Many tests were performed so as to calibrate the biosensor for its selectivity, using different initial values of bacteria ($N_0$). *E. coli* 0157:H7 available commercially in lyophilized form was reconstituted with 1.0 mml of phosphate buffer saline solution , pH 7.4, and inoculated in various Petri dishes containing MacConkey sorbitol agar base, supplemented with glycerol at 0.2%. The incubation was at 35° C. for a period of 24 hours. After this period, the purity of the material was confirmed and the Petri dishes were stocked at 4° C., for later dilution. For obtaining the dilutions with $N_0$=10, 20, 30, 40, 50, 60, 70 and 80 microorganisms used 100 $\mu$l of phosphate buffer saline solution (pH 7.4) and for values of $N_0$ 90, 100, 200, 400 and 800 microorganisms, the volume used was 500 $\mu$l of phosphate buffer saline solution (pH 7.4). For each sample the cells were counted using a Coulter (Beckman) counter that permits an accuracy of ±1%. Finally, the sensitive probe of Example 1 was inserted in the Petri dishes containing the media described above, in a dilution with a known number of microorganisms and the measurement of points was initiated with the use of systems adequate for the measurement/acquisition of data known to experts in the field.

EXAMPLE 4

Correlation of the Growth With the Estimated Number of Bacteria

Figure 2:
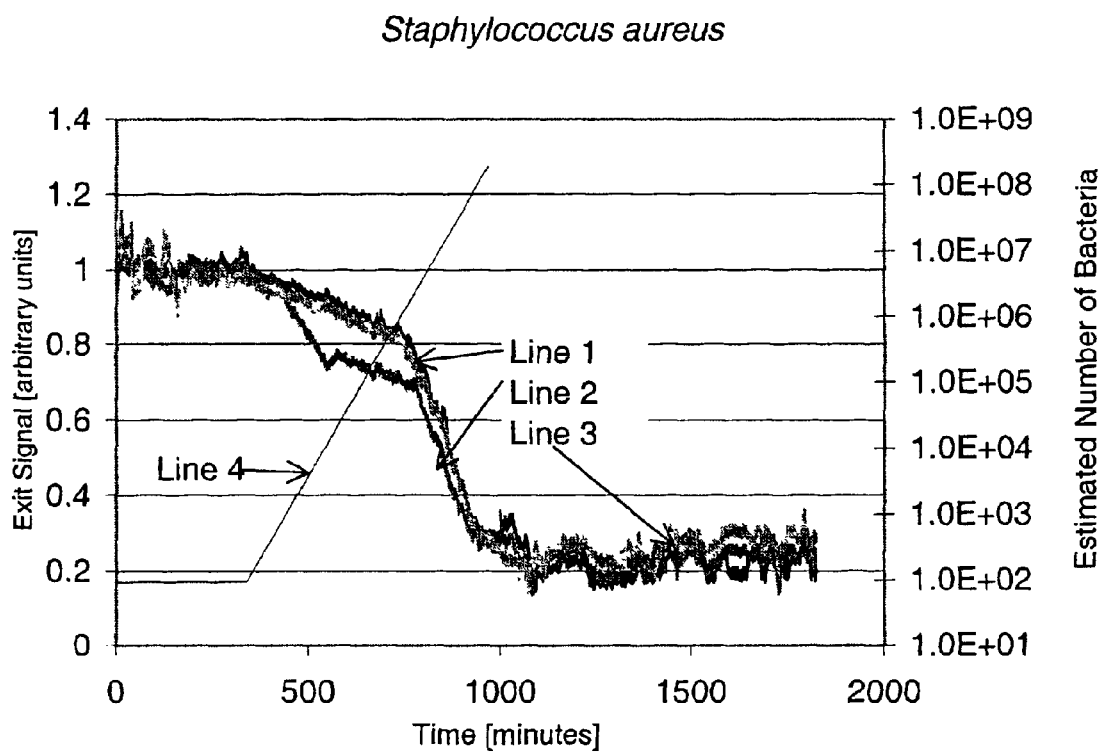
FIG. 2: Shows the exit signals of the optical sensor with *Staphylococcus aureus* resistant to methicillin. Lines 1, 2 and 3 represent the exit signal and line 4 concerns the estimated number of bacteria.
Figure 3:
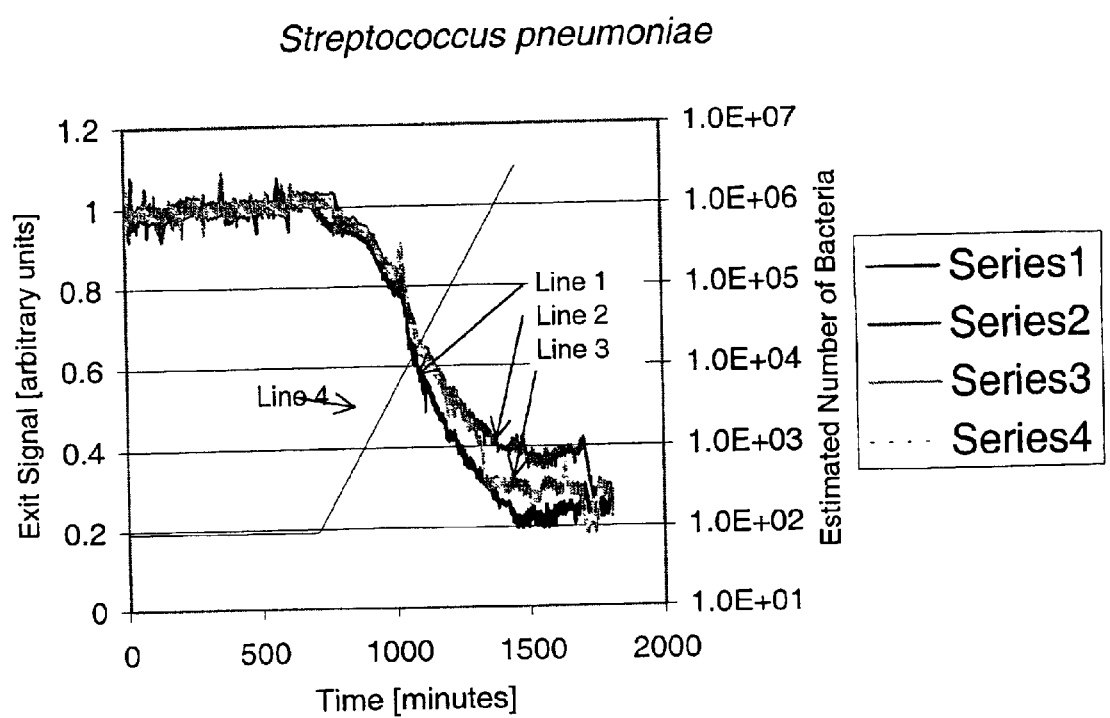
FIG. 3: Shows the exit signals of the optical sensor with *S. pneumoniae*. Lines 1, 2 and 3 represent the exit signal and line 4 concerns the estimated number of bacteria.

FIGS. 2 and 3 present, respectively, the optical signal of the sensor for *Staphylococcus aureus* resistant to methicillin and *S. pneumoniae*. Lines 1, 2 and 3 represent the output signal for samples 1, 2 and 3, respectively. Line 4 correlates the growth with the estimated number of bacteria, in accordance with the following formula:

$$N(t) = N_0 2^{t/GT}$$

where t is the time in minutes, N is the total number of bacteria in the time t, No is the initial number of bacteria (equal to 94 for *Staphylococcus aureus* resistant to methicillin (MRSA) and 91 for *S. pneumoniae*) and GT is the time of generation (equal to 30 minutes for MRSA and 48 minutes for *S. pneumoniae*).

Observing FIGS. 2 and 3, one notes the presence of three distinct phases: the first is a plateau where no response is detected (Lag phase). The result for *Staphylococcus aureus* resistant to methicillin and *S. pneumoniae* demonstrate a lag phase of, approximately, 6 and 13 hours respectively. This different is due to the different times of generation for each microorganism, in other words, 30 minutes for *Staphylococcus aureus* resistant to methicillin and 48 minutes for *S. pneumoniae*. The second region presents a negative inclination. This is the phase of exponential growth of the bacteria. The third phase is characterized by a saturation of the volume that occurs around the sensitive fiber. This is not yet the stationary phase of the culture, since it continues to grow for a total period of 48 hours.

EXAMPLE 5

Characterization of the Sensitivity of the Biosensor

Figure 4:
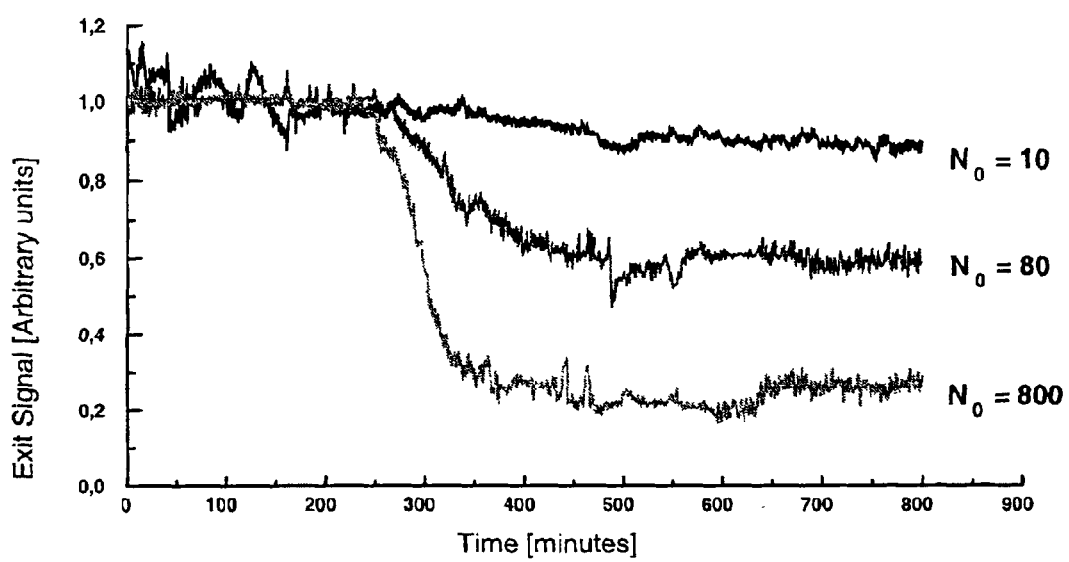
FIG. 4: Presents data for the temporal optical response of the biosensor with *E. coli* 0157:H7.

Various measurements were performed with the aim of characterizing the sensitivity of the biosensor, each one during an interval of 24 hours (1440 minutes) employing 13 different values of colony forming units (CFU) or initial number of bacteria ($N_0$)). These values vary from 10 to 800 for samples of *E. coli* 0157:H7. FIG. 4 plots the data of the temporal optical response, $I_{(out)}(t)$ (in arbitrary units) of three of these measurements ($N_0$=10, 80 and 800). The results of the optical measurements are reproducible. The reproduction is also observed in all the measurements corresponding to the different values of $N_0$ (Lag phase, Log phase and stationary phase). In the first phase of bacterial growth, a level DC $I_{(out)}(t)=I_{Lag}$ is observed with approximately the same temporal variation. The level $I_{Lag}$ is related to the response of the biosensor, in which *E. coli* 0157:H7 remains in its lag phase during the time of the $\Delta t_{Lag}$ decrease.

Figure 5:
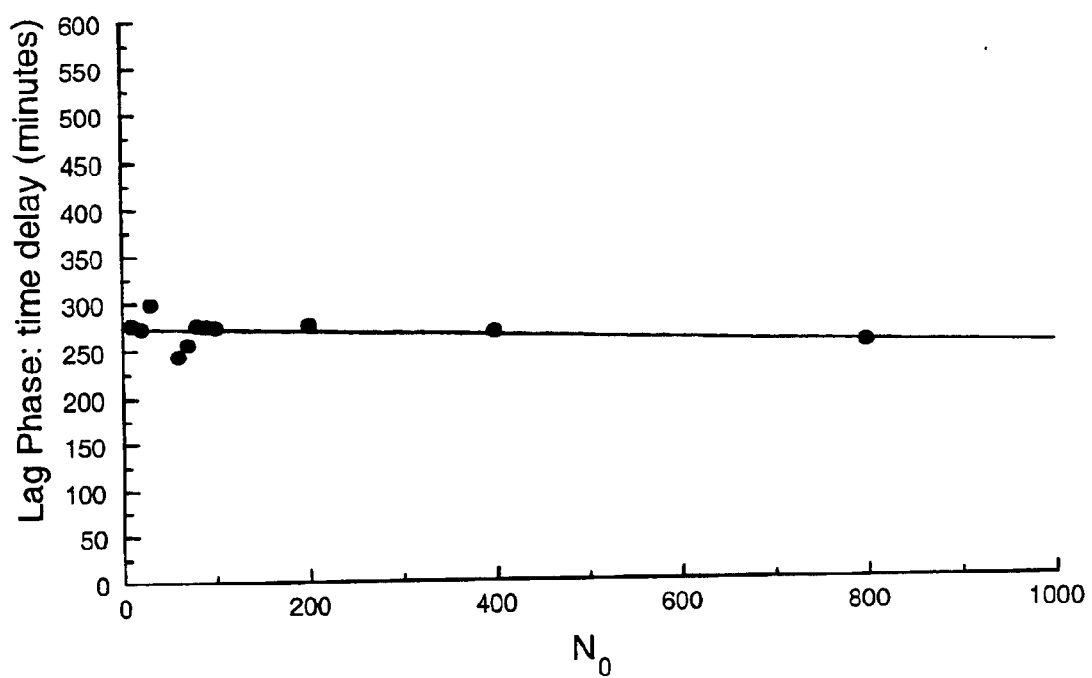
FIG. 5: Shows the time of remaining in the Lag phase versus the initial number of bacteria *E. coli* 0157:H7.

FIG. 5 shows a plot, for all the measurements of the $\Delta t_{Lag}$ data versus $N_0$. The linear ratio with practically no angular coefficient was field out with an average of 270±4 minutes or, approximately 4.5 hours, represents a reproducibility of about 1.5%. $\Delta t_{Lag}$ is attributed to the temporal variation that *E. coli* 0157:H7 consumes in its Lag phase independent of its initial number, $N_0$.

The optical attenuation $\Delta I_{out}$ (in dB) for each $N_0$ signifies the difference between the variation of time $\Delta t_{Log}$ (in hours) of the Log phase, for each $N_0$. The derivative of the time $\beta_{Log}$ of $I_{out}(t)$, in the Log phase, varies with $N_0$ and can be calculated by the following formula:

$$\beta_{Log}(N_0) = \Delta I_{out}/\Delta t_{Log}.$$

Figure 6:
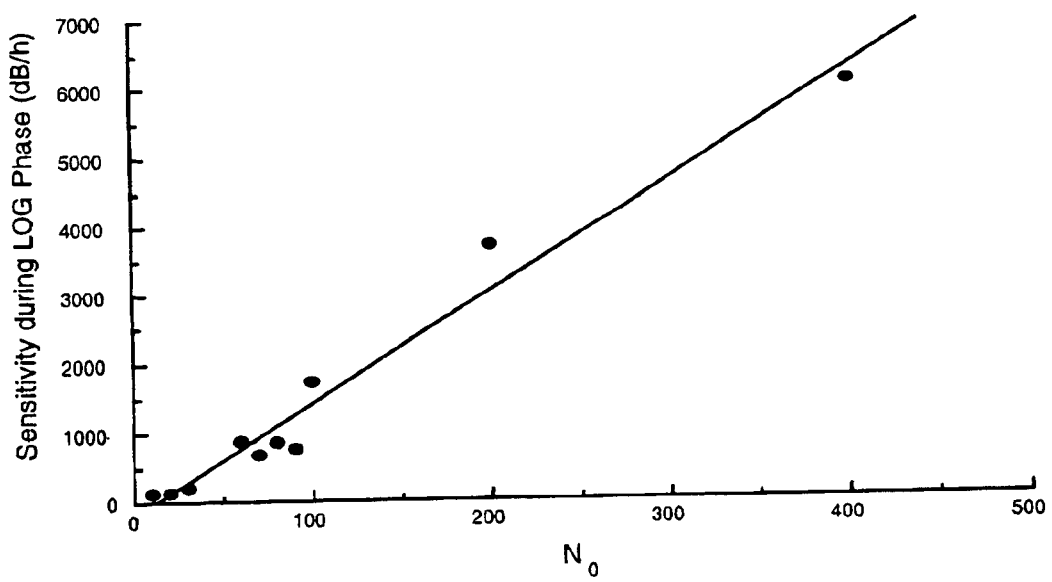
FIG. 6: Shows data for the sensitivity of the biosensor during the Lag phase.
Figure 7:
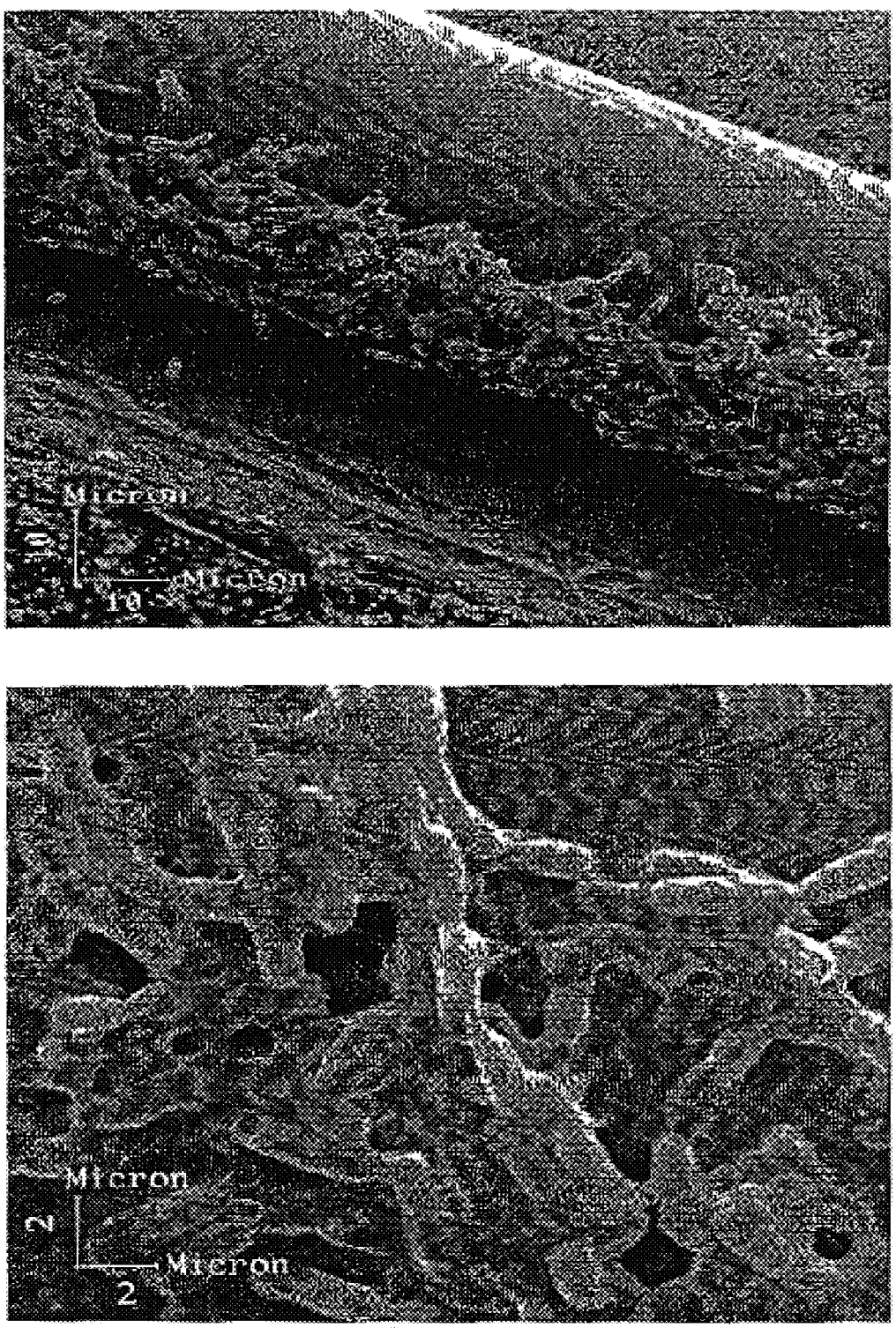
FIG. 7: Shows a photograph obtained by electronic microscopy of *E. coli* 0157:H7 (Lag phase) in physical contact with the optical fiber.
Figure 8:
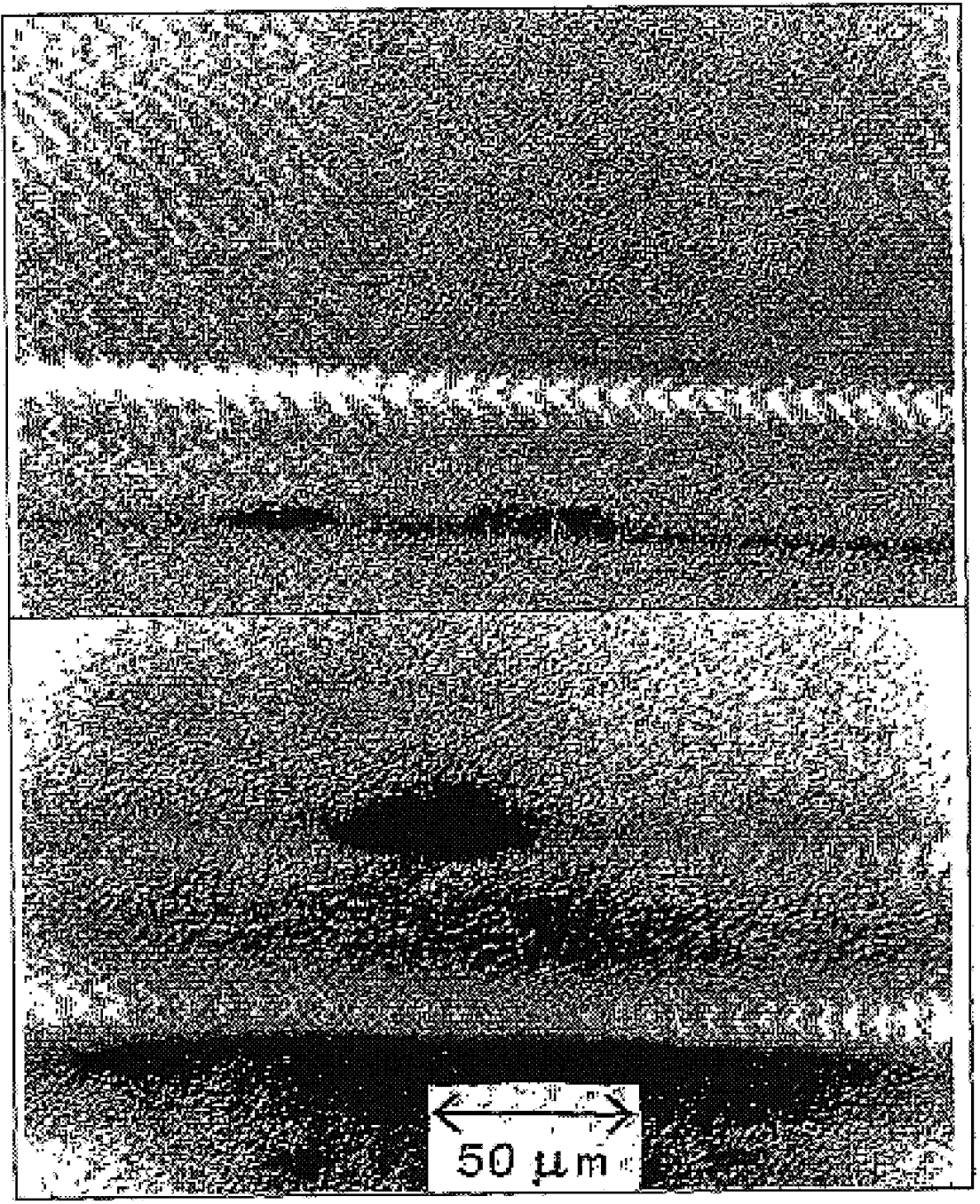
FIG. 8: Shows a photograph obtained by optical microscopy by phase contrast of *E. coli* 0157:H7.

FIG. 6 demonstrates the sensitivity of the biosensor $\beta_{Log}$ (dB/hour), during the Log phase, when the initial number of bacteria varies from $N_0$=10 to $N_0$=400. The linear correlation coefficient of 0.985 provides a straight line for the calibration curve:

$\beta_{Log}(N_0)=(\Delta\beta_{Log}/\Delta N_0)N_0$. The calculated angular coefficient is $\Delta\beta_{Log}/\Delta N_0=(0,016\pm0,001)$ (dB/hour)/bacteria. Thus, the response speed of the biosensor during the Log phase increases in 0.016 dB/hour, for each *E. coli* 0157:H7 inoculated in the Petri dish. For $N_0$=800, the angular coefficient $\beta_{Log}(800)$~dB/h. Therefore, it is possible to infer from the output signal the initial number of bacteria measuring the angular coefficient of the Log phase. The number of colony forming units is directly related to the degree of contamination of the sample. FIGS. 7 and 8 show photographs obtained by electronic microscopy of *E. coli* 0157:H7 (Log phase) in physical contact with an optical fiber and with a phase contrast optical microscopy of *E. coli* 0157:H7, respectively.

What is claimed is:

1. Method for detecting contamination by specific microorganisms in a sample, comprising:
   (a) exposing an evanescent-field of a sensitive fiber optic by removing at least a portion of a primary covering of and reducing a thickness of a sheath of said fiber optic;
   (b) contacting the exposed evanescent-field with a sample to be examined, with said sample having a form adequate so as to generate an optical signal in response to the presence of microorganisms in the sample;
   (c) demodulating the optical signal generated in stage (b) and using this value to quantify the microorganisms.

2. Method in accordance with claim 1 wherein said reducing of the thickness of the sheath of said optical fiber for stage (a) includes chemical etching performed with a strong acid.

3. Method in accordance with claim 2 wherein the strong acid is hydrofluoric acid.

4. Method in accordance with claim 3 wherein a time of chemical etching and a concentration of the hydrofluoric acid are adjusted in a manner to permit the etching of the sheath of the fiber optic until it approaches a thickness of 0.5 to 1 $\mu$m from a core of said fiber optic.

5. Method in accordance with claim 4 wherein the time of said chemical etching is 11 minutes and the concentration of the acid is 38%.

6. Method in accordance with claim 1 wherein the sample to be examined is in a support containing a culture medium appropriate to permit the growth of microorganisms.

7. Method in accordance with claim 6 wherein the support is a Petri dish containing Agar medium and specific nutrients.

8. Method in accordance with claim 6 wherein reactants are incorporated to the culture medium capable of altering the properties of the culture medium in a manner as to permit a better detection of an index of refraction of the microorganisms.

9. Method in accordance with claim 6 wherein the sensitive fiber has integrated to itself one or more concentric layers of a material selected from the group consisting of dielectricals, metallics, superconductors or semiconductors in a manner so as to alter the transversal spatial distribution of the evanescent-field and thus optimizing the contact with the medium containing the specific microorganism.

10. Method in accordance with claim 1 wherein the sensitive fiber has integrated to itself one or more concentric layers of a material selected from the group consisting of dielectricals, metallics, superconductors or semiconductors in a manner so as to alter the transversal spatial distribution of the evanescent-field and thus optimizing contact with a medium containing the specific microorganism.

11. Method in accordance with claim 10 wherein the material is a polymer selected from a group consisting of polyvinyl chloride, polyurethanes, polyureas and polyesters.

12. Method in accordance with claim 1 further comprising monitoring contamination by specific microorganisms in real time.

13. Device for surveying microorganisms through insertion of a sensitive fiber optic, with an adequately exposed evanescent-field, into a surface or volume of a biological culture medium specific for a microorganism to be detected, comprising a system for demodulation based on a fiber optic circuit including:

an optical source; a 2×1 fiber optic coupling; a 2×2 fiber optic coupling; a first optical fiber extension termed sensitive element containing a first polarization controller, a segment of sensitive optical fiber with exposed evanescent-field being in direct physical contact with a biological culture medium and a first extremity from which light exits to a first photodetector; a second optical fiber extension termed reference element containing a second polarization controller, and a second extremity from which light exits to a second photodetector in a manner as to compose a device that functions based on modulation of light intensity (or amplitude).

14. Device in accordance with claim 13 wherein the sensitive optical fiber contains a Bragg grating engraved within its core in a manner as to compose a device that functions based on the modulation of the length of the light wave.

15. Device in accordance with claim 13 wherein the sensitive optical fiber consists of a high birefringency fiber of the type that maintains polarization in such a manner as to compose a device that functions based on the modulation of the polarization of light.

16. Device in accordance with claim 13 wherein the sensitive optical fiber consists of a high birefringency fiber of the type that maintains polarization containing a Bragg grating engraved within its core in a manner as to compose a device that functions based on the modulation of the length of the light wave and/or light polarization.

17. Device for surveying microorganisms through insertion of a sensitive fiber optic, with an adequately exposed evanescent-field, into a surface or volume of a biological culture medium specific for a microorganism to be detected, comprising a system for demodulation based on a fiber optic circuit including:

an optical source; a 2×1 fiber optic coupling; a 2×2 fiber optic coupling; a first optical fiber extension termed sensitive element containing a first polarization controller, two connection links, a segment of sensitive optical fiber with exposed evanescent-field being in direct physical contact with a biological culture medium and having two semi-reflective extremities, a first extremity from which light exits to a first photodetector; a second optical fiber extension termed reference element containing a second polarization controller, and a second extremity from which light exits to a second photodetector in a manner as to compose a device that functions based on modulation of a complete phase of light of a Fabry-Perot type interferometer.

18. Device in accordance with claim 17 wherein the sensitive optical fiber contains a Bragg grating engraved within its core in a manner as to compose a device that functions based on the modulation of the length of the light wave.

19. Device in accordance with claim 17 wherein the sensitive optical fiber consists of a high birefringency fiber of the type that maintains polarization in such a manner as to compose a device that functions based on the modulation of the polarization of light.

20. Device in accordance with claim 17 wherein the sensitive optical fiber consists of a high birefringency fiber of the type that maintains polarization containing a Bragg grating engraved within its core in a manner as to compose a device that functions based on the modulation of the length of the light wave and/or light polarization.

21. Device for surveying microorganisms through insertion of a sensitive fiber optic, with an adequately exposed evanescent-field, into a surface or volume of a biological culture medium specific for the microorganism to be detected, comprising a system for demodulation based on a fiber optic circuit including:

an optical source; a 2×1 fiber optic coupling; a 2×2 fiber optic coupling; a first optical fiber extension termed sensitive element containing a first polarization controller, a segment of sensitive optical fiber with exposed evanescent-field being in direct physical contact with a biological culture medium, and a first extremity of reflective optical fiber; a second extension of optical fiber termed reference element containing a second polarization controller and a second extremity of reflective optical fiber; a third extremity of optical fiber from which light exits to a first photodetector and a fourth extremity of optical fiber from which light exits to a second photodetector in a manner as to compose a device that functions based on modulation of a complete light phase of a Michelson type interferometer.

22. Device in accordance with claim 21 wherein the sensitive optical fiber contains a Bragg grating engraved within its core in a manner as to compose a device that functions based on the modulation of the length of the light wave.

23. Device in accordance with claim 21 wherein the sensitive optical fiber consists of a high birefringency fiber of the type that maintains polarization in such a manner as to compose a device that functions based on the modulation of the polarization of light.

24. Device in accordance with claim 21 wherein the sensitive optical fiber consists of a high birefringency fiber of the type that maintains polarization containing a Bragg grating engraved within its core in a manner as to compose a device that functions based on the modulation of the length of the light wave and/or light polarization.

25. Device for surveying microorganisms through insertion of a sensitive fiber optic, with an adequately exposed evanescent-field, into a surface or volume of a biological culture medium specific for a microorganism to be detected, comprising a system for demodulation based on a fiber optic circuit including:

an optical source; a 2×1 fiber optic coupling; a first 2×2 fiber optic coupling; a first optical fiber extension termed sensitive element containing a first polarization controller, a segment of sensitive optical fiber with an exposed evanescent-field in direct physical contact with a biological culture medium, a first extremity of optical fiber directly linked to a second extremity of optical fiber belonging to a second 2×2 fiber optic coupling; and a third extremity of optical fiber from which light exits to a first photodetector; a second extension of optical fiber termed reference element containing a second polarization controller and a fourth extremity of optical fiber directly linked to a fifth extremity of optical fiber belonging to said second 2×2 fiber optic coupling, and a sixth extremity of optical fiber from which light exits to a second photodetector in a manner as to compose a device that functions based on modulation of a complete light phase of a Mach-Zehnder type interferometer.

26. Device in accordance with claim 25 wherein the sensitive optical fiber consists of a high birefringency fiber of the type that maintains polarization in such a manner as to compose a device that functions based on the modulation of the polarization of light.

27. Device in accordance with claim 25 wherein the sensitive optical fiber consists of a high birefringency fiber of the type that maintains polarization containing a Bragg grating engraved within its core in a manner as to compose a device that functions based on the modulation of the length of the light wave and/or light polarization.

* * * * *